United States Patent [19]

Johnson

[11] 4,172,835

[45] Oct. 30, 1979

[54] 1-(PHENYLAMINO)PYRROLE

[75] Inventor: Robert E. Johnson, East Greenbush, N.Y.

[73] Assignee: Sterling Drug Inc., New York, N.Y.

[21] Appl. No.: 970,550

[22] Filed: Dec. 18, 1978

Related U.S. Application Data

[60] Continuation-in-part of Ser. No. 908,468, May 22, 1978, which is a division of Ser. No. 730,162, Oct. 7, 1976, Pat. No. 4,138,405, which is a division of Ser. No. 585,448, Jun. 9, 1975, Pat. No. 4,051,147, which is a continuation-in-part of Ser. No. 372,324, Jun. 21, 1973, abandoned.

[51] Int. Cl.² .......................................... C07D 207/50
[52] U.S. Cl. .................................. 260/326.9; 424/274
[58] Field of Search ....................................... 260/326.9

[56] References Cited

U.S. PATENT DOCUMENTS

| | | | |
|---|---|---|---|
| 2,725,378 | 11/1955 | Reed | 260/313.1 |
| 4,051,147 | 9/1977 | Johnson | 260/326.9 |
| 4,138,405 | 2/1979 | Johnson | 260/326.9 |

*Primary Examiner*—Donald G. Daus
*Assistant Examiner*—Mary Lee
*Attorney, Agent, or Firm*—William G. Webb; B. Woodrow Wyatt

[57] ABSTRACT

1-(Phenylamino)pyrrole, useful as a urinary antiseptic, hypotensive and hypoglycemic agent, is prepared by reaction of an N-benzoylphenylhydrazine or N-lower-alkanoylphenylhydrazine or a lower-alkanealdehyde N-benzoylphenylhydrazone or N-lower-alkanoylphenylhydrazone with a 2,5-di-lower-alkoxytetrahydrofuran followed by hydrolytic removal of the benzoyl or lower-alkanoyl group from the resulting N-benzoyl-1-(phenylamino)pyrrole or N-lower-alkanoyl-1-(phenylamino)pyrrole.

1 Claim, No Drawings

1-(PHENYLAMINO)PYRROLE

RELATED APPLICATIONS

This is a continuation-in-part of my prior, copending application Ser. No. 908,468, filed May 22, 1978, which is a division of my prior, copending application Ser. No. 730,162, filed Oct. 7, 1976, now U.S. Pat. No. 4,138,405 patented Feb. 6, 1979 which is a division of my prior application Ser. No. 585,448, filed June 9, 1975, now U.S. Pat. No. 4,051,147, patented Sept. 27, 1977, copending with application Ser. No. 730,162, which is a continuation-in-part of my prior application, Ser. No. 372,324, filed June 21, 1973, copending with application Ser. No. 585,448, and now abandoned, the disclosures of all of which are incorporated herein by reference.

BACKGROUND OF THE INVENTION (a) Field of the Invention

This invention relates to 1-(phenylamino)pyrrole useful as a urinary antiseptic, hypotensive and hypoglycemic agent.

(b) Description of the Prior Art

The compound, 1-phenylamino-2,5-dimethylpyrrole, is described by Reed U.S. Pat. No. 2,725,378 (patented Nov. 29, 1955 on an application filed Sept. 19, 1951) as an intermediate for the preparation of monomethine cyanine dyes and is not known to have any other utility than as an intermediate. As disclosed hereinbelow, I have found this compound to be inactive as a hypotensive or hypoglycemic agent and to have only slight activity as an antibacterial agent.

SUMMARY OF THE INVENTION

In a composition of matter aspect, the invention relates to the species, 1-(phenylamino)pyrrole, useful as a urinary antiseptic, hypotensive and hypoglycemic agent.

DETAILED DESCRIPTION OF THE INVENTION

More specifically, this invention relates to the species, 1-(phenylamino)pyrrole, which is useful as a urinary antiseptic, hypotensive and hypoglycemic agent, and having the formula:

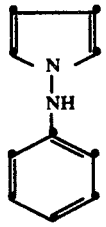

I

The compound of the invention is prepared either by reaction of an N-benzoylphenylhydrazine or N-lower-alkanoylphenylhydrazine of formula II or a lower-alkanealdehyde N-benzoylphenylhydrazone or N-lower-alkanoylphenylhydrazone of formula III with a 2,5-di-lower-alkoxytetrahydrofuran of formula IV followed by hydrolysis of the resulting N-benzoyl-1-(phenylamino)pyrrole or N-lower-alkanoyl-1-(phenylamino)pyrrole of formula Ia in order to effect removal of the N-benzoyl or N-lower-alkanoyl group.

The methods are illustrated by the following reactions:

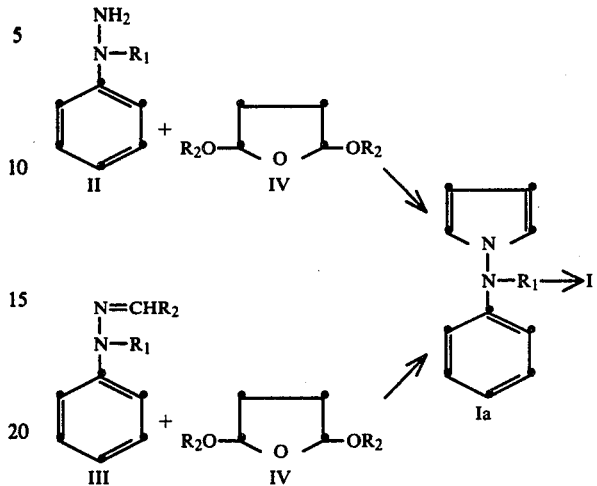

where $R_1$ represents benzoyl or lower-alkanoyl, and $R_2$ represents lower-alkyl. The initial reaction between the compounds of formula II or formula III and the 2,5-di-lower-alkoxytetrahydrofuran of formula IV is preferably carried out in an acid medium, for example a lower-alkanoic acid such as acetic acid. Although the reaction takes place at ambient temperature, the reaction rate is increased at elevated temperatures, and therefore it is advantageous to carry out the reaction at temperatures from 50° C. to approximately 100° C. The hydrolysis of the compounds of formula Ia to the final product of formula I is carried out by heating a solution of the compound of formula Ia in a lower-alkanol, for example methanol, ethanol or isopropanol, in the presence of at least one molar equivalent of an alkali metal hydroxide, for example sodium hydroxide or potassium hydroxide, and isolating the product from an alkaline medium.

The compound of formula I has been found active in the urinary antisepsis test, thus indicating usefulness of this species as a urinary antiseptic agent. The urinary antisepsis test is described briefly as follows: Female, Sprague-Dawley rats weighing from 160 to 200 grams were divided into groups of three and placed in plastic metabolism cages. Each group received 50 mg./kg. of the test compound at 8:00 a.m. and 50 mg./kg. at 4:00 p.m. The compound was suspended in gum tragacanth at a concentration which would allow the oral administration of 1 ml. of suspension for each 100 g. weight of the rat. The urine from each group of rats was collected for twenty-four hours starting at the time of the first medication. At the end of the collection period, the samples were measured, centrifuged for clarification, sterilized by ultrafiltration and frozen in sealed vials at −20° C. until they were thawed for testing against each of the bacterial and fungal organisms: *Staphylococcus aureus* Smith, *Escherichia coli* Vogel, *Proteus mirabilis* MGH-1, *Klebsiella pneumoniae* 39645, *Pseudomonas aeruginosa* MGH-2, *Trichophyton mentagrophytes*, *Aspergillus niger* and *Candida albicans*. Antibacterial activity of the urine samples was determined on the Autotiter ® by serial, two-fold dilutions of the urine in tryptose phosphate broth to which the bacterial inoculum was added. Dilutions of from 1:2 through 1:16,384 were tested. The inoculum was prepared by diluting an eighteen hour broth culture to a 0.1 optical density before diluting to 1:250 in tryptose phosphate broth. To indicate bacterial growth, 50 mcg./ml. of triphenyltetrazolium chloride was added to the inoculum, and after incubation at 37° C. for eighteen hours, those solutions in which bacterial growth had taken place showed a color change from colorless to red. The highest dilution without color change was recorded as the inhibitory dilution, and activity at the 1:2 dilution was not considered significant. Activity was considered to reside in dilutions at 1:4 or greater.

The compound of the invention was also found to be active as an antihypertensive agent on oral administration in spontaneously hypertensive rats. The spontaneously hypertensive rat (SHR) is a strain of genetically hypertensive animals developed from Wistar rats by Okamoto et al., Jap. Circ. J., 27, 282–293 (1963) after selective inbreeding. Unlike any other hypertensive animal model, the SHR requires no surgical intervention, and it is widely recognized as the closest model to essential hypertension in man. Furthermore, the hypertension in these rats is not due to any of the known causes of secondary hypertension, and the blood pressure increases progressively with age. Complications often observed in human essential hypertension such as cardiac, renal and vascular changes are also observed in the SHR. The procedure used is described as follows: The compound to be screened is tested in five SHR's whose base line blood pressure has been determined earlier in the day. The test compound is given orally at a single daily dose suspended in 1% gum tragacanth in a total volume of 1 ml./kg., and systolic blood pressure measurements are obtained at 2, 6 and 24 hours after administration of the test compound using a photoelectric tensometer (ankle rubber cuff method) as described by Kersten et al., J. Lab. Clin. Med. 32, 1090–1098 (1947). Alternatively the test compound is administered at single daily oral doses of 50 mg./kg. for twelve consecutive days, and blood pressure determinations are made, as before, each day at 2, 6 and 24 hours after medication. A control group run side by side in each study received only the gum tragacanth.

The compound of the invention has also been found to have hypoglycemic activity in the alloxan and streptozotocin-induced diabetes model in rats. In the latter test procedures, diabetes was produced in male, Sprague-Dawley rats weighing approximately 150 g. by the administration of either alloxan monohydrate, 160 mg./kg. (s.c.), or streptozotocin, 65 mg./kg. (i.v.), after an overnight fast. Fasting blood glucose levels were obtained once each week for three weeks using a modification of the procedure described by Hoffman, J. Biol. Chem. 120, 51(1937) which involves the measurement of the reduction of yellow ferricyanide ion to colorless ferrocyanide by glucose. Animals having fasting blood glucose levels of >250 mg./dl. for the last two weeks were distributed into groups such that all groups in a test had a similar distribution and mean fasting blood glucose level. Normal rats were similarly distributed on the basis of a single fasting blood glucose level. The test compound was suspended in 1% gum tragacanth and administered orally in 5 ml./kg. twice a day. One group in each test was given 1% gum tragacanth as a control, and fasting blood glucose levels were determined for each group at weekly intervals.

The actual determination of the numerical biological data definitive for the compound of the invention is readily made by standard test procedures by technicians versed in biological test procedures, without the need for any extensive experimentation.

The compound of the invention can be formulated for use by preparing a dilute solution in an organic medium in which the compound is soluble, for example ethyl alcohol, or in such solution containing a surfactant, and is applied to a surface to be disinfected by conventional methods such as spraying, swabbing, immersion, and the like. Alternatively, the compound can be formulated as ointments or cream bases, for example alkylpolyether alcohols, cetyl alcohol, stearyl alcohol, and the like, or as jellies by incorporating the compound in conventional jelly bases such as glycerol and tragacanth. It can also be formulated for use as aerosol sprays or foams or in conventional carriers, including sugars such as sucrose, lactose or maltose, for oral administration as tablets or capsules.

The molecular structure of the compound of the invention was assigned on the basis of study of its infrared, ultraviolet, and NMR spectra, and confirmed by the correspondence between calculated and found values for elementary analyses for the elements.

The following examples will further illustrate the best mode of preparing the compound of the invention. All melting points are uncorrected.

EXAMPLE 1

A solution of 24.8 g. (0.10 mole) of N-benzoyl-N-phenylhydrazine hydrochloride, 13.2 g. (0.10 mole) of 2,5-dimethoxytetrahydrofuran and 8.2 g. (0.10 mole) of anhydrous sodium acetate in 100 ml. of glacial acetic acid was heated on a steam bath for one hour, then cooled, concentrated to a small volume in vacuo and diluted with about 150 ml. of 2 N sodium hydroxide. The mixture was extracted with 300 ml. of ethyl acetate, and the combined extracts were washed with saturated sodium bicarbonate solution until the washes were basic, dried over anhydrous magnesium sulfate and taken to dryness to give 25.7 g. of solid material which was recrystallized with charcoaling from cyclohexane to give 19.5 g. of 1-(N-benzoyl-N-phenylamino)pyrrole, m.p. 109°–110° C.

The latter (19.0 g., 0.073 mole) was dissolved in a solution containing 9.0 g. (0.16 mole) of powdered potassium hydroxide in 200 ml. of methanol, and the solution was heated under reflux for two hours, concentrated in vacuo to a volume of about 25 ml. and then poured into about 200 ml. of water. The mixture was extracted twice with 100 ml. portions of hexane, and the combined extracts were washed with water, dried over anhydrous magnesium sulfate, and taken to dryness to give 11.4 g. of material which was recrystallized from pentane to give 9 g. of 1-(phenylamino)pyrrole, m.p. 44°–46° C.

EXAMPLE 2

Reaction of 104 g. (0.96 mole) of phenylhydrazine with 47 g. (1.07 mole) of acetaldehyde in 500 ml. of diethyl ether while maintaining the temperature at less than 5° C. and evaporation of the solution to dryness afforded 134 g. of acetaldehyde phenylhydrazone as an oil which was crystallized from pentane to give 116 g. of solid having m.p. 81°–90° C. Reaction of the latter with 122 g. (0.86 mole) of benzoyl chloride in 300 ml. of pyridine and recrystallization of the product from ethanol/water afforded 75.6 g. of acetaldehyde N-benzoylphenylhydrazone, m.p. 91°–93° C. Reaction of the latter (70.0 g., 0.315 mole) with 41.5 g. (0.315 mole) of 2,5-dimethoxytetrahydrofuran in 300 ml. of glacial acetic acid using the procedure described above in Example 1 gave 79.5 g. of 1-(N-benzoyl-N-phenylamino)-pyrrole which (85.5 g., 0.325 mole), on hydrolysis with 400 ml. of methanolic potassium hydroxide (26 g., 0.4 mole) using the procedure described above in Example 1, afforded 45.5 g. of 1-(phenylamino)-pyrrole as an oil which was crystallized from hexane (m.p. 43°-45° C.).

BIOLOGICAL TEST RESULTS

Data obtained in the urinary antiseptic test procedure described above, expressed in terms of inhibitory dilutions, are given in Table A below, where the letter "I" designates inactive. For comparative purposes, data similarly obtained for the known compound, 1-(phenylamino)-2,5-dimethylpyrrole designated hereinafter "Ref.", are also given. In certain instances, results obtained in one test did not accord with results obtained in a second or third test, and data obtained in such multiple tests are given for each organism where inconsistent results were obtained.

Table A

| Organism | Compound I | Ref. |
|---|---|---|
| (a) Staph. aureus Smith | 1:24; 1:128 | 1:8; I;I |
| (b) E. coli Vogel | 1:2; 1:4 | I |
| (c) Kleb. pneumoniae 39645 | I | I |
| (d) Prot. mirabilis MGH-1 | 1:4; 1:192 | I |
| (e) Prot. vulgaris 9920 |  | I; 1:2 |
| (f) Ps. aeruginosa MGH-2 | 1:2 | I |
| (g) Strep. pyogenes C203 |  | 1:2 |
| (h) C. albicans 10231 | I | 1:2 |
| (i) As. niger 16404 |  | 1:2; I |
| (j) T. mentagrophytes 9129 | I | 1:2; 1:4 |

In in vitro antibacterial tests using the procedure described by Goss et al., Applied Microbiology, 16 (No. 9), 1414–1416 (1968), both compound I and the reference species were found to be inactive against each of organisms (a), (b), (c), (d) and (f) above.

Both compound I and the reference compound were found to be inactive on single oral administration in the SHR model, the former given at doses of 50 and 200 mg./kg. and the latter at 150 mg./kg., compound I producing a decrease of, respectively, 4 and 16 mm. Hg in blood pressure and the reference compound producing a decrease of 22 mm. Hg at the indicated doses. However, when administered at a single daily dose of 50 mg./kg. for twelve consecutive days, compound I produced a marked and sustained decrease in blood pressure that approached 30–40 mm. Hg toward the end of the first week and which became quite evident during the second week when decreases in blood pressure in the range from 60–80 mm. Hg were noted. This hypotensive effect was reversible on termination of medication. On the other hand, the reference compound, when administered at the same dose and in the same chronic regimen, produced very little blood pressure lowering.

Compound I has also been found to have hypoglycemic activity in the alloxan and streptozotocin-induced diabetic rat model. Data so obtained in these test procedures are given in Tables B (alloxan model) and C (streptozotocin model). Results are expressed in terms of fasting blood glucose levels in mg./dl. ± standard error, and the percent change ($\Delta\%$), i.e. the difference, expressed as percent, between blood glucose levels in control animals (administered 1% gum tragacanth at 0.5 mg./100 g. body weight) and medicated animals, was calculated only when a statistically significant difference over control was obtained.

Table B

| | Weeks | | | | | | | | |
|---|---|---|---|---|---|---|---|---|---|
| | 1 | | | 2 | | | 3 | | |
| | Hours Post Medication | | | | | | | | |
| Medication | 0 | 3 | 6 | 0 | 3 | 6 | 0 | 3 | 6 |
| 1% G.T. | 325 ± 30 | 348 ± 32 | 322 ± 31 | 352 ± 14 | 380 ± 11 | 383 ± 9 | 352 ± 17 | 388 ± 17 | 376 ± 12 |
| Cpd. I(50 mg./kg.) ($\Delta\%$) | 299 ± 32 | 263 ± 32 | 277 ± 31 | 220 ± 32* (−38%) | 165 ± 27** (−57%) | 119 ± 14** (−69%) | 185 ± 34** (−47%) | 148 ± 38** (−62%) | 139 ± 39** (−63%) |

Here and elsewhere the notations * and ** mean:
*Statistically different from control at $p < 0.01$
**Statistically different from control at $p < 0.001$ Table C

| | Weeks | | | | | | | | |
|---|---|---|---|---|---|---|---|---|---|
| | 1 | | | 2 | | | 3 | | |
| | Hours Post Medication | | | | | | | | |
| Medication | 0 | 3 | | 0 | 3 | 6 | 0 | 3 | 6 |
| 1% G.T. | 357 ± 11 | 378 ± 9 | 378 ± 5 | 358 ± 12 | 366 ± 5 | 353 ± 12 | 354 ± 11 | 386 ± 6 | 378 ± 5 |
| Cpd.I (12.5mg./kg.) | 344 ± 10 | 356 ± 17 | 336 ± 24 | 345 ± 7 | 344 ± 9 | 311 ± 22 | 335 ± 6 | 337 ± 11 | 309 ± 26 |
| Cpd.I (25 mg./kg.) $\Delta\%$ | 323 ± 11 | 294 ± 20* (−22%) | 252 ± 34** (−33%) | 278 ± 24* (−22%) | 237 ± 33* (−35%) | 196 ± 37* (−44%) | 292 ± 27 | 254 ± 37* (−34%) | 216 ± 45* (−43%) |
| Cpd.I(50 mg./kg.) $\Delta\%$ | 335 ± 8 | 282 ± 17** (−25%) | 236 ± 30** (−38%) | 278 ± 29 | 202 ± 37** (−45%) | 217 ± 41* (−39%) | 203 ± 33** (−43%) | 147 ± 22** (−62%) | 121 ± 24** (−68%) |
| 1% G.T. | 319 ± 9 | 341 ± 8 | 336 ± 9 | 355 ± 13 | 355 ± 12 | 375 ± 6 | 336 ± 11 | 353 ± 8 | 389 ± 21 |
| Ref. (50 mg./kg.) $\Delta\%$ | 324 ± 6 | 326 ± 6 | 322 ± 11 | 302 ± 24 | 287 ± 25 | 277 ± 31* (−26%) | 339 ± 7 | 346 ± 6 | 347 ± 5 |

The compound of the invention also has been found to have a hyperglycemic effect when administered to normal (i.e. non-diabetic) rats as shown by the data in Table D below. As before, results are expressed in terms of fasting blood glucose levels in mg./dl. ± standard error, and the percent change ($\Delta\%$) is the difference, expressed as percent, between blood glucose levels in control animals (administered 1% gum tragacanth at 0.5 mg./100 g. body weight) and blood glucose levels in medicated animals, the $\Delta\%$ being determined only when a statistically significant difference over control was obtained.

Table D

| Medication | Weeks | | | | | | | | |
|---|---|---|---|---|---|---|---|---|---|
| | 1 | | | 2 | | | 3 | | |
| | Hours Post Medication | | | | | | | | |
| | 0 | 3 | 6 | 0 | 3 | 6 | 0 | 3 | 6 |
| 1% G.T. | 87 ± 3 | 90 ± 2 | 89 ± 2 | 89 ± 1 | 91 ± 2 | 90 ± 2 | 91 ± 3 | 96 ± 2 | 103 ± 2 |
| Cpd. I(50 mg./kg.) Δ% | 93 ± 5 | 106 ± 6 | 103 ± 6 | 125 ± 4** (+40%) | 132 ± 3** (+45%) | 123 ± 5** (+37%) | 132 ± 2** (+45%) | 129 ± 6** (+34%) | 137 ± 4** (+33%) |

I claim:

1. 1-(Phenylamino)pyrrole.

* * * * *